United States Patent [19]

Clark

[11] 4,269,177
[45] May 26, 1981

[54] THERAPEUTIC DEVICE

[76] Inventor: Stanley M. Clark, 8049 Robin La., Brecksville, Ohio 44141

[21] Appl. No.: 67,112

[22] Filed: Aug. 16, 1979

[51] Int. Cl.$^3$ ............................................ A61H 15/00
[52] U.S. Cl. ........................................ 128/57; 128/60
[58] Field of Search ............... 128/165, 38, 40, 44, 128/51, 57, 60, 64, 67, 294, 53, DIG. 20

[56]  References Cited

U.S. PATENT DOCUMENTS

| 2,091,131 | 8/1937 | Cone | 128/57 |
|---|---|---|---|
| 2,531,074 | 11/1950 | Miller | 128/38 |
| 2,699,165 | 1/1955 | Ferrier | 128/60 |
| 2,747,570 | 5/1956 | Jobst | 128/60 |
| 2,781,041 | 2/1957 | Weinberg | 128/60 |
| 3,128,761 | 4/1964 | Smith | 138/58 |
| 3,450,450 | 1/1969 | Hopkins et al. | 312/1 |
| 3,862,629 | 1/1975 | Rotta | 128/64 X |
| 4,013,069 | 3/1977 | Hasty | 128/64 X |
| 4,191,177 | 3/1980 | Abbott | 128/57 X |

Primary Examiner—Stephen C. Pellegrino
Attorney, Agent, or Firm—Sherman & Shalloway

[57] ABSTRACT

A tubular inflated bag is progressively rolled onto a limb thereby applying continuous pressure to the limb. The bag is initially located about a tubular support and the limb to be treated is located axially parallel with respect to the support. An outer sleeve surrounds the tubular bag and is progressively moved toward the limb. As the sleeve moves toward the arm, the progress of the sleeve causes the bag to roll onto the limb progressively applying pressure to the limb. The progress of the sleeve is twice as fast as the progress of the bag. Therefore, the sleeve may be telescoping or collapsible so that the sleeve does not unnecessarily limit the movement of the bag.

14 Claims, 10 Drawing Figures

THERAPEUTIC DEVICE

BACKGROUND OF THE INVENTION

1. Field of the Invention

This invention relates to that class of therapeutic devices which are used to treat edematose conditions or other circulatory malfunctions of human limbs and to methods of treating such conditions.

2. Description of the Prior Art

Heretofore edema and certain other circulatory problems of the limbs have been treated by the application of external counter pressures to the affected limb, usually by means of inflatable, stocking-like sleeves which are either specifically tailored to fit a particular limb or which are adjustable, as by lacing, to fit the limb. Once fitted onto the limb they are inflated to a given pressure to exert a squeezing action on the limb. One form of sleeve may be unitary in construction, comprising a single cell, see U.S. Pat. No. 2,747,570. Other forms may be multi-celled with perhaps four or five sets of separate cells extending along its length, see for example, U.S. Pat. Nos. 2,781,041 and 2,531,074. In multi-celled forms the separate cells can be inflated to the same or different pressures. However, in many instances the separate cells are sized to accommodate for the different girths of various parts of a limb such as the ankle, calf and thigh portions of a leg and are inflated to exert equal pressures throughout the limb. Other forms of pressure stockings or sleeves have similar or related modes of operation.

These prior art devices do not readily accommodate to limbs of varying dimensions. Many of them must be individually fitted to a patient. They are also limited as to the method by which they apply pressures to a limb. None of them apply a uniformly progressive pressure; that is, a pressure which is applied progressively and smoothly from the outer extremity of a limb along the limb towards the body while maintaining a uniform pressure upon all parts of the limb once such pressure is applied.

The present invention enables such a pressure to be applied to a limb from its other extremity progressively upon the limb in the direction of the body thereby urging fluids to move from the limb into the torso. This is accomplished by providing an inflated bag which is rolled into contact with a limb from the extremity of the limb longitudinally and inwardly along the limb until at the end of the rolling movement the entire limb is enveloped by the bag which exerts a uniform, predetermined pressure upon the limb.

The specific manner in which this is accomplished can be best understood from a consideration of one preferred form of the invention which is described specifically with respect to the treatment of a human arm which is afflicted with edema, but it will be appreciated that the same principles will generally apply to the treatment of a leg that is similarly afflicted and to the treatment of other conditions in which it is desirable to promote circulation and otherwise to assist in the removal of bodily fluids from a human limb.

DETAILED DESCRIPTION OF THE INVENTION

Figure 1:
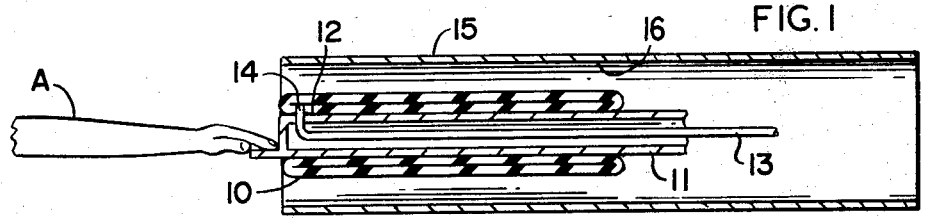
FIG. 1 is a somewhat diagrammatic, fragmentary, longitudinal, sectional view of a preferred form of the invention with the bag in deflated condition, showing its relationship to a human arm which is to be treated.

In describing the invention, the term "inwardly" is used to indicate a direction from the outer extermity, i.e., from the hand or foot, towards the body; the term "outwardly" is used to indicate a direction away from the body towards the hand or foot. The phrase "to expel the fluids from the limb" means to move fluids from the limb into or towards the body; that is, from an outer, or lower, portion of the limb into an upper portion of the limb. It is to be understood, of course, that "expel" does not mean the complete removal of fluids rather it means the expulsion of some of the fluids, such as the excess fluid which is present in conditions of edema.

The invention applies the desired pressure to a limb, in this instance, a human arm, indicated at A, by means of an inflatable, flexible, relatively thin-walled, bag 10 which takes the form of an elongated, closed tube, having an inner diameter approximating the wrist dimension of the arm which is to be treated and a length somewhat greater than the total length of the arm. The bag may be of rubber or any suitable elastomer and may be suitably reinforced by fabric to control its shape, all as well understood in the art. The bag 10 is mounted on a cantilever support 11, and in its deflated condition has a close fit on and about the cantilever support 11. An annular portion 12 at the left end of the bag is secured as by a suitable cement to the support 11 but except for this limited area of attachment, the remainder of the bag is not attached to the support 11 at any other point and as will be seen, can be rolled free of the support. The support 11 preferably is tubular to permit an air conduit 13 to extend through the bore of the support to connect with the interior of the bag through an opening 14 which extends through the wall of the bag at the annulus 12. The air conduit 13 is connected to a suitable source of air under pressure or to a hand or foot pump, not shown. A suitable gauge, also not shown, can be provided to measure the inflation pressure.

The inflated bag 10 is moved longitudinally upon the support 11 by means of an external, cylindrical, supporting sleeve 15 which is mounted so that it may be moved into the position shown in FIG. 1, coaxial with and enclosing the bag 10. The manner in which support sleeve 15 is supported and moved longitudinally into its various operative positions will be described later.

Figure 2:
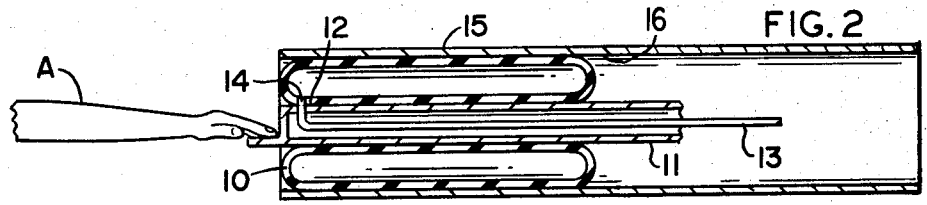
FIG. 2 is a view similar to FIG. 1 in which the bag is initially inflated and in position to be rolled leftwardly to exert pressure upon the arm.

When the bag 10 is inflated by passing air under pressure through opening 14, the bag expands outwardly into contact with the inner surface 16 of the external support sleeve 15, see FIG. 2. Thus, the external support sleeve confines the outward expansion of the bag 10.

Figure 3:
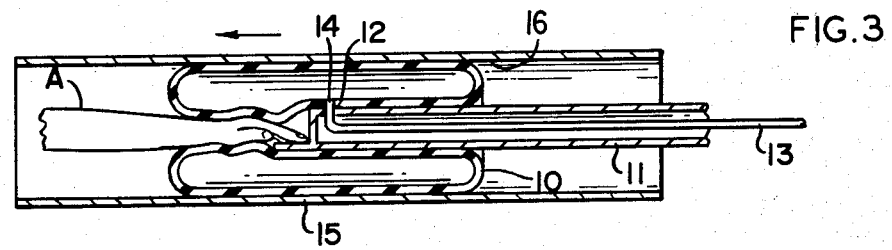
FIG. 3 is a view similar to FIGS. 1 and 2 showing the apparatus in an intermediate position with the inflated bag partially rolled upon the arm.
Figure 4:
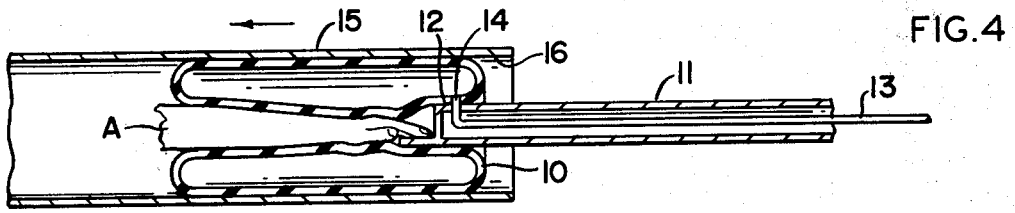
FIG. 4 is a view similar to FIGS. 1-3 in which the inflated bag is fully rolled upon the arm and is exerting pressure upon the arm for virtually its entire length.

In use, the patient holds his arm so that it is substantially coaxial with the support 11 and the bag 10, with his hand positioned adjacent the end of the bag, see FIG. 1. The bag 10 is then inflated into frictional contact with the inner surface 16 of the support sleeve 15, see FIG. 2. The support sleeve 15 is moved to the left as viewed, and as it does so the inflated bag is carried to the left by virtue of frictional contact of the bag with the surface 16 of sleeve 15 with the bag rolling progressively from the support 11 and onto the arm. An intermediate position of the sleeve 15 is shown in FIG. 3. Since the left end of the bag is fixed at 12 to the support 11, the leftward movement of the sleeve causes the bag to roll leftwardly and inwardly, since it is confined against outward expansion by the support sleeve 15. The bag as it moves upon the arm exerts a uniform fluid pressure on the arm A substantially equal to the inflation pressure of the bag. As shown in FIG. 4, at the conclusion of the leftward movement of the sleeve 15 the bag has been carried leftwardly for substantially its full length, at which time it envelops substantially the entire length of the arm A and applies a predetermined uniform pressure upon every surface of the arm A.

Figure 8:
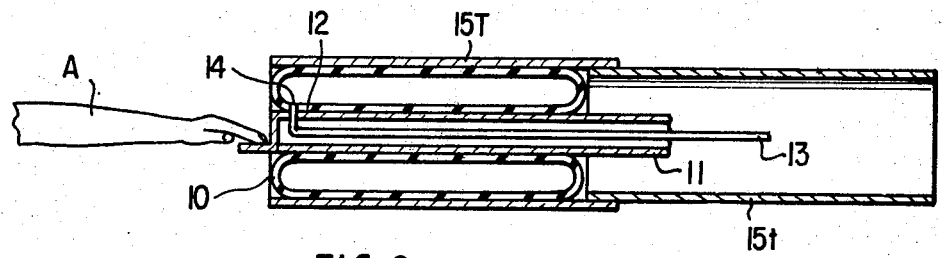
FIGS. 8, 9 and 10 are longitudinal, sectional views of another embodiment of the invention wherein the sleeve has a telescoping configuration.
Figure 9:
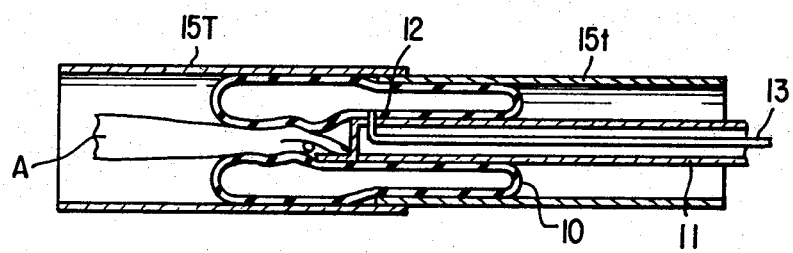
Figure 10:
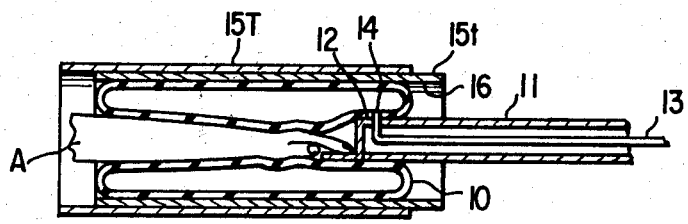

It is apparent that as the sleeve 15 moves toward the limb to be treated, the progress of the sleeve will be limited by its forward edge striking the torso. If only partial treatment of the limb is desired, this limitation will not effect the treatment of the limb by the invention. However, in situations where treatment of the entire limb is desired, it is contemplated that the sleeve may take a telescoping configuration as shown in FIGS. 8, 9 and 10.

For convenience and clarity, the sleeve is illustrated as having portions 15T and 15t. However, it is also contemplated that the sleeve may be formed of three or more telescoping sections. It is preferable that the inner sleeve 15t is located on the side of outer sleeve 15T opposite the limb-engaging end. As shown in FIG. 9, as the sleeves are moved toward the limb A, the bag rolls onto the limb A and from the outer sleeve 15T to the inner sleeve 15t. Eventually, the entire bag is located within the inner sleeve 15T as shown in FIG. 10. The outer sleeve 15T may then be collapsed or telescoped onto the inner sleeve 15T to allow for further movement of the sleeves and bag 10.

Figure 5:
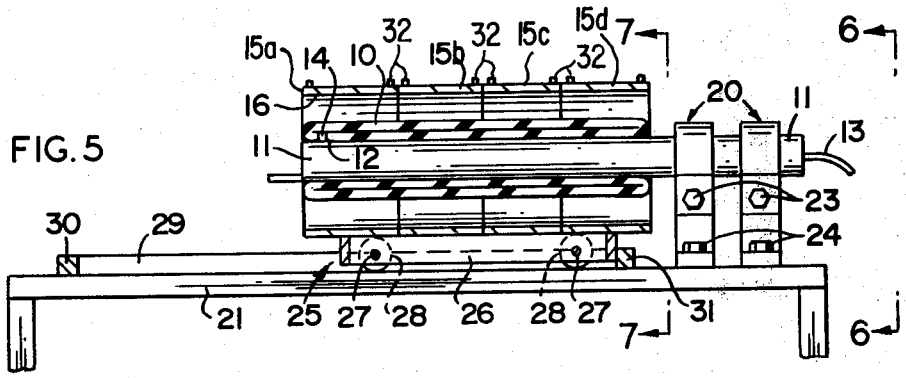
FIG. 5 is a longitudinal view, similar to FIG. 1, partially in section showing one form of supporting means for another embodiment of the invention.

Alternatively, the sleeve may be constructed of multiple longitudinally hinged sections as shown in FIG. 5. These sections 15a, 15b, 15c, and 15d are adjacently, axially arranged so that the forward portion 15a of the sleeve can be manually removed as the sleeve is moved toward the limb. Similarly, succeeding forward sections may be removed section by section to allow continued movement of the sleeve until the arm A is fully enveloped by the bag 10. Depending on the length of the sleeve and the length of the limb being treated, it is contemplated that a removed section may be replaced at the rearward end of the sleeve, if necessary.

Moreover, once the bag pressure is applied to any portion of the arm A, that pressure is maintained against that portion inasmuch as that portion of the inflated bag which initially is rolled inwardly into contact with the arm continues to press inwardly upon the arm. Since the application of the force progresses inwardly along the arm in the direction of the shoulder, bodily fluids tend to be urged out of the arm ahead of the edge of the inwardly rolling bag toward the shoulder and since the pressure is maintained on the arm, once it is applied, there are no pockets of low pressure to the rear, i.e., outwardly, of the rolling, forward edge of the bag and, hence, there is no tendency for any substantial backflow of bodily fluids behind the rolling edge of the bag. Since the pressure within the bag is a fluid pressure, the pressure over the entire surface of the arm will be uniform regardless of variations in cross section along the arm. Thus, the device need not be tailored to variations in arm size, for the manner in which the pressure is imposed automatically accommodates for all variations.

In use, the pressures can be varied throughout a particular stroke of the rolling bag. Thus initally the pressure in the bag as it presses against the hand and wrist could be $P_1$ and as the bag rolls over the forearm the pressure could be increased to a new pressure $P_2$ and then when the bag reaches the upper arm it could be further increased to $P_3$. Conversely the pressure can be progressively decreased as the rolling cycle takes place. The bag can be easily rolled back and forth in repeated cycles while the pressure is held constant or varied as desired. Thus a great flexibility in the mode of treatment is provided.

Figure 6:
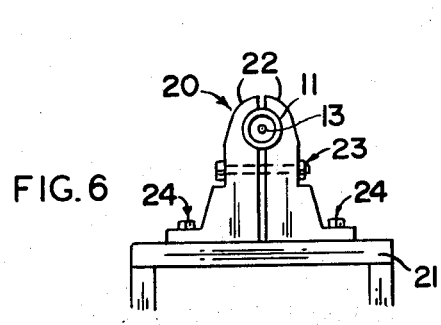
FIG. 6 is a partial end view of the apparatus of FIG. 5 showing the clamping supports for the cantilever support.

There are various ways in which the cantilever support 11 and the external sleeve 15 can be mounted for operation. One such construction is shown in FIG. 5, in which the internal support 11 with the bag 10 supported thereon is supported in cantilever fashion at its right end, as viewed, by a pair of identical clamping supports, indicated generally at 20, which are secured to and supported by a table 21. Each clamping support takes the form of a pair of jaws 22, concavely recessed to receive and grip the support 11 as shown in FIG. 6. The jaws 22 are drawn together so as to grip the tube firmly by the nut and bolt arrangement indicated at 23 and the jaws are secured to the table 21 by the nut and bolt arrangement shown at 24.

Figure 7:
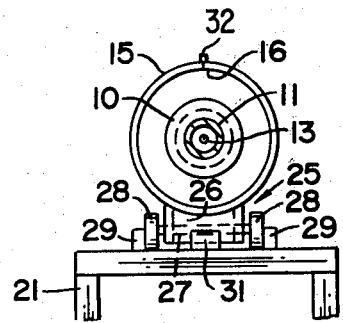
FIG. 7 is a sectional view of the apparatus of FIG. 5 taken in the plane 7—7 of FIG. 5.

The external support 15 is mounted on a carriage indicated generally 25, and comprises a bed portion 26 to which support 15 is secured by any suitable means, not shown, but which could be a strong cement, or by brazing if the parts are metallic, or by a suitable clamping arrangement. The lower portion of carriage bed 26 is drilled to receive the axles 27 of wheel and axle arrangement shown in FIGS. 5 and 7. Wheels 28 which are journalled on the axles 27 support the carriage for movement left and right, as viewed, along the table.

The movement of the carriage back and forth on the table is guided by a pair of parallel rails 29 fixed to the table which define the desired path of carriage travel by engaging the sides of wheels 28. Stops 30 and 11 fixed to the table limit the leftward and rightward movements, respectively, of the carriage. The assembly of carriage and external support 11 can be moved manually along the table, although if desired suitable power means such as a hydraulic cylinder and piston unit, or a rotatable threaded shaft and nut arrangement driven by a motor or any other means for providing reciprocal movement of the carriage may be employed.

Obviously the particular means of supporting the bag 10 and the external supporting sleeve 15 and of moving them with relation to the limb to be treated, so long as the described function is accomplished, may take many different forms. For hospital use, the construction could be simple and susceptible to manual operation and control.

Furthermore, while only one bag has been shown and described, two or more smaller bags which together will envelop the limb to be treated might be employed. The bags could be inflated with hot or cold fluids and, as indicated, the pressures and the duration of application can be varied within wide limits. Moreover, while the bag 10 has been described as a closed tube which is cemented to the internal support at 12, it could be an open tube terminating in special reinforced edges which would be clamped into place on the support.

I claim:

1. A method of urging bodily fluids to flow from a limb into the body which comprises the steps of:
   initially applying a fluid pressure to the limb at a first area remote from the body: and
   thereafter applying a continuous rolling fluid pressure from said first area progressively to successive adjacent areas of the limb closer to the body until a substantial portion of the limb has been subjected to said progressive rolling fluid pressure.

2. The method of claim 1 further including the step of maintaining said pressure on the successive adjacent areas of the limb after the pressure is initially applied thereto while said application of rolling fluid pressure proceeds over the limb towards the body.

3. The method of claim 2 further including the step of thereafter releasing said fluid pressure on the limb progressively in a direction from an area adjacent the body toward the more remote areas of the limb until the pressure is completely released from the limb.

4. The method of claim 3 in which the steps of applying, maintaining and releasing said fluid pressure to the limb are repeated in a cyclic fashion.

5. The method of claim 1 in which the steps of initially applying and thereafter applying fluid pressure to the limb are repeated in a cyclic fashion.

6. An apparatus to promote circulation within a limb and to urge excess fluids to flow from the limb towards the body, said apparatus comprising: an inflatable, flexible bag; means to inflate said bag: means restraining the radially outward expansion of the bag in its inflated condition: means for moving said bag longitudinally relative said limb: means for rolling said bag inwardly upon itself as said relative longitudinal movement takes place to produce a rolling edge, thereby exerting an inward, rolling pressure upon the limb and urging fluids in the limb to move ahead of said rolling edge in the direction of the body.

7. The apparatus according to claim 6 in which said restraining means comprises an external support extending parallel to said bag and said limb, and means to position said external support about said bag as the bag is inflated so that an inner surface of the support will restrain the expansion of the bag, said inner surface making frictional contact with said expanded bag whereby movement of said external support longitudinally with respect to said limb carries the expanded bag by virtue of said frictional contact in a rolling movement upon and along said limb.

8. The apparatus according to claim 7, in which said bag is tubular and is mounted on and secured to the free end of a cantilever support and is secured to said cantilever support at a point adjacent the free end thereof and in which said external support comprises a sleeve co-axial with said cantilever support and said bag, said sleeve being moveable longitudinally with respect to said cantilever support to carry said expanded bag in a rolling movement from said cantilever support onto the limb.

9. The apparatus according to claim 6 or 8 wherein the means to inflate said bag includes a means for increasing the pressure within said bag as the bag is rolled onto the limb.

10. The apparatus according to claim 8 wherein the sleeve is comprised of a plurality of telescoping members.

11. The apparatus according to claim 8 wherein the sleeve is comprised of a plurality of longitudinally hinged sections.

12. An apparatus for exerting pressure upon a portion of a limb comprising:
   (a) base support means;
   (b) cantilever support;
   (c) means for supporting said cantilever support parallel to said base support;
   (d) a tubular bag located about said cantilever support and attached at one point thereto;
   (e) sleeve means coaxially located about said bag and said cantilever support;
   (f) means for sliding said sleeve means along said base support means; and
   (g) means for inflating said bag.

13. An apparatus for exerting pressure upon a portion of the human body comprising an inflatable bag, means to inflate said bag with fluid under pressure, means to maintain said bag in an inflated condition, means to limit outward expansion of said bag when the bag is inflated, and means to cause said bag to roll inwardly and progressively upon said body portion to exert and maintain a substantially uniform pressure upon the body portion.

14. A method of urging bodily fluids to flow from a limb into the body which comprises the steps of:
   initially applying a fluid pressure to the limb at a first area remote from the body
   thereafter applying a continuous rolling fluid pressure from said first area progressively to successive adjacent areas of the limb closer to the body until a substantial portion of the limb has been subjected to said progressive rolling fluid pressure; and
   maintaining said pressure in the successive adjacent areas of the limb after the pressure is initially applied thereto while said application of rolling, fluid pressure proceeds over the limb towards the body,
   wherein the steps of initially applying, thereafter applying, and maintaining said fluid pressure are comprised of the steps of
   providing a tubular inflated bag having an axial opening therein;
   locating the limb to be treated in a position coaxial with respect to the tubular bag; and
   urging the tubular bag axially toward the limb so that the bag rolls onto the limb.

* * * * *